United States Patent
Pattipaka et al.

(10) Patent No.: US 10,677,903 B2
(45) Date of Patent: Jun. 9, 2020

(54) METHODS AND APPARATUS FOR REDUCING A TRANSIENT GLITCH IN ULTRASOUND APPLICATIONS

(71) Applicant: Texas Instruments Incorporated, Dallas, TX (US)

(72) Inventors: Ravikumar Pattipaka, Bangalore (IN); Raja Sekhar Kanakamedala, Bangalore (IN); Aravind Miriyala, Bangalore (IN); Vajeed Nimran P A, Bangalore (IN); Sandeep Kesrimal Oswal, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 778 days.

(21) Appl. No.: 15/367,982

(22) Filed: Dec. 2, 2016

(65) Prior Publication Data
US 2018/0156903 A1 Jun. 7, 2018

(51) Int. Cl.
| | | |
|---|---|---|
| G01S 7/52 | (2006.01) | |
| A61B 8/00 | (2006.01) | |
| A61B 8/08 | (2006.01) | |

(52) U.S. Cl.
CPC ........ *G01S 7/52077* (2013.01); *A61B 8/4483* (2013.01); *A61B 8/5269* (2013.01)

(58) Field of Classification Search
CPC ........ G01S 15/18; G01S 15/93; G01S 15/931; G01S 7/527; G01S 7/5273; G01S 7/529; G01S 7/524; G01S 7/52077; G01B 17/00; A61B 8/4483; A61B 8/5269
USPC ................................................... 73/602, 631
See application file for complete search history.

(56) References Cited

U.S. PATENT DOCUMENTS

| | | | | |
|---|---|---|---|---|
| 3,458,854 | A * | 7/1969 | Murphree | G01S 15/8902 367/101 |
| 5,777,238 | A * | 7/1998 | Fletcher-Haynes | G01F 1/667 73/861.31 |
| 9,595,949 | B2 * | 3/2017 | Amit | H03K 17/0814 |
| 2011/0063011 | A1 * | 3/2011 | Barlow | H01L 29/0692 327/328 |
| 2013/0154715 | A1 * | 6/2013 | Choy | H03K 17/063 327/390 |
| 2016/0183917 | A1 * | 6/2016 | Kameishi | A61B 8/4483 600/437 |
| 2019/0201933 | A1 * | 7/2019 | Li | B06B 1/0215 |

FOREIGN PATENT DOCUMENTS

WO WO-2018044489 A9 * 3/2019 ........... G01S 7/5202

\* cited by examiner

*Primary Examiner* — Lisa M Caputo
*Assistant Examiner* — Rose M Miller
(74) *Attorney, Agent, or Firm* — John R. Pessetto; Charles A. Brill; Frank D. Cimino

(57) ABSTRACT

Methods and apparatus for reducing a transient glitch in ultrasound applications are disclosed. An example apparatus includes a transducer to (A) output a signal during a transmit phase and (B) receive a reflected signal corresponding to the signal during a receive phase; a receiver switch coupled to the transducer at a first node, the receiver switch to (A) open during the transmit phase and (B) close during the receive phase; and a clamp coupled to the transducer at the first node, the clamp to provide a high impedance during the transmit phase and the receive phase and provide a low impedance during a transient phase.

13 Claims, 5 Drawing Sheets

METHODS AND APPARATUS FOR REDUCING A TRANSIENT GLITCH IN ULTRASOUND APPLICATIONS

FIELD OF THE DISCLOSURE

This disclosure relates generally to ultrasound devices and, more particularly, to methods and apparatus for reducing a transient glitch in ultrasound applications.

BACKGROUND

An ultrasound system front end (e.g., ultrasound front ends) is a system that converts a high voltage electrical signal to a high frequency audio signal which reflects off an object creating an echo. The ultrasound system front end receives the echo and converts the echo into an image (e.g. a sonogram). An ultrasound front end may be used in a variety of applications. For example, an ultrasound front end may be used to generate images (e.g., two dimensional or three dimensional) of an object, identify structural defects in an object, detect impurities of an object, and/or detect abnormalities in living bodies.

SUMMARY

Examples disclosed herein reduce a transient glitch in ultrasound applications. An example apparatus includes a transducer to (A) output a signal during a transmit phase and (B) receive a reflected signal corresponding to the signal during a receive phase. The example apparatus further includes a receiver switch coupled to the transducer at a first node, the receiver switch to (A) open during the transmit phase and (B) close during the receive phase. The example apparatus further includes a clamp coupled to the transducer at the first node, the clamp to provide a high impedance during the transmit phase and the receive phase and provide a low impedance during a transient phase.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
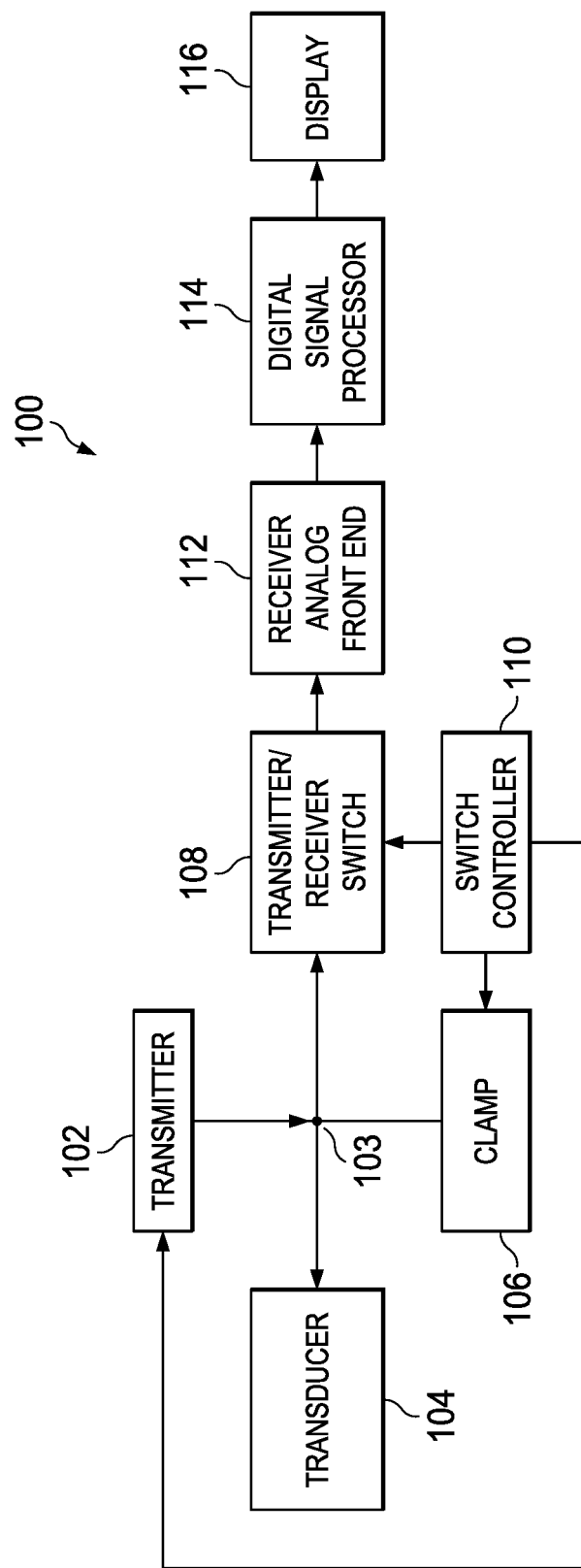
FIG. 1 is an illustration of an example ultrasound front end for reducing a transient glitch.

An ultrasound front end includes a transmitter, a transducer, and a receiver. When the ultrasound front end is used to image an object, the transmitter uses a voltage pulse(s) to drive the transducer to generate and output a signal (e.g., a high frequency audio signal) at an object. After the transmitter drives the transducer, the receiver receives the signal output by the transducer after being reflected off the object (e.g., an echo). Because the transmitter generates high voltage (e.g., 180 volts (V) peak-to-peak) and the receiver is sensitive and, therefore, capable of detecting and processing much smaller voltages (e.g., 500 millivolts (mV) peak-to-peak), ultrasound front ends also include a transmit/receive (T/R) switch. The T/R switch is a high voltage isolation switch coupled between the transmitter and the receiver to protect the receiver during a transmit phase of the ultrasound front end.

When an ultrasound front end transitions from transmitting mode (e.g., the transmitter generating the high voltage to drive the transducer) to receiving mode (e.g., receiving the echo), the T/R switch is enabled (e.g., about 1 microsecond (us)) after the transmitter finishes pulsing. However, enabling and/or disabling the T/R switch and/or the transmitter generates a glitch at a transducer node (e.g., a node coupled to the T/R switch, the transmitter, and the transducer). A glitch is an undesired voltage spike and/or voltage abnormality produced when a circuit transitions from on to off (via a switch). The glitch can excite the transducer to produce unwanted second transmits, thereby degrading the image quality generated by the ultrasound front end.

Conventional ultrasound front ends couple a pair of anti-parallel diodes between the transmitter and the transducer. The anti-parallel diodes generate a high impedance transmitter in receiver mode. The high impedance reduces loading of high voltage transistor parasitics during the receive phase, thereby reducing the loss in received signal. Additionally, the anti-parallel diodes reject unwanted glitches from the transmitter. However, such anti-parallel diodes at the transmitter of such conventional ultrasound front ends include a diode recovery issue causing unwanted current in a reverse direction. Thus, such anti-parallel diodes cause low amplitude distortion. Additionally, conventional ultrasound front ends do not power down the transmitter when the transmitter is not being used (e.g., the transmitter is always active) to avoid an additional power up and/or power down glitch. Maintaining transmitter power corresponds to high power consumption. Examples disclosed herein alleviate such conventional ultrasound front ends by providing a high impedance transmitter in the receiving phase without the anti-parallel diodes, thereby improving low-amplitude distortion. Examples disclosed herein further include dynamically powering up and/or powering down the transmitter when the transmitter is not pulsing without an extra glitch on the transducer, thereby decreasing the power consumption of the ultrasound front end. Using examples disclosed herein, the current glitch is reduced from 50 mV (e.g., corresponding to the conventional ultrasound front end) to 15 mV.

Examples disclosed herein include series diodes embedded in the transmitter that are biased with quiescent current. Examples disclosed herein generates a high impedance transmitter without causing low amplitude distortion. Examples disclosed herein further includes power down/up switches embedded in the transmitter to power down the transmitter when the transmitter is not transmitting a signal, thereby reducing power consumption. Conventionally, powering on and/off the transmitter in itself causes a glitch. Examples disclosed herein diminish such a glitch by including a clamp at a node between the transmitter, the transducer, and the T/R switch. The clamp provides a very low impedance path to ground during transition states (e.g., transitioning the transmitter and/or the T/R switch from on to off or vice versa) to discharge the glitch. The clamp disclosed herein is capable of handling positive and negative 100 V swing during transmit phase and provides a high impedance during transmit and/or receive phases (e.g., non-transition states) to reduce signal distortion. Additionally, the clamp disclosed herein absorbs any glitches associated with enabling and/or disabling the clamp itself.

FIG. 1 is a circuit diagram of an example ultrasound front end 100 disclosed herein to reduce a transient glitch. The example ultrasound front end 100 includes an example transmitter 102, an example transducer node 103, an example transducer 104, an example clamp 106, an example transmitter/receiver (T/R) switch 108, an example switch controller 110, an example receiver analog front end (AFE) 112, an example digital signal processor 114, and an example display 116.

The example transmitter 102 of FIG. 1 is a circuit including both active and passive components to generate a high voltage (e.g., positive or negative 100 voltage) pulse and/or series of pulses. The example transmitter 102 is powered on to generate the pulse(s) and powered down after the pulse(s) have been generated so that the example receiver analog front end 112 can receive a response to the pulse(s). As further explained in conjunction with FIG. 2, the example transmitter 102 includes series diodes providing a high impedance during a receive phase and power up/down switches to conserve power during the receive phase. The example transmitter 102 outputs the high voltage pulse(s) to the example transducer 104 via the example transducer node 103.

The example transducer 104 of FIG. 1 receives the high voltage pulse(s) from the example transmitter 102 via the transducer node 103 and generates a signal (e.g., an audio signal) corresponding to the pulse(s). The example transducer 104 may include piezoelectric transducer and/or capacitive transducers to convert the electric pulse(s) into sound. The sound is output by the transducer 104 to reflect off of an object. The transducers and/or sensors receive the reflected signal (e.g., echo) after being reflected off of the object. In some examples, the example ultrasound front end 100 determines a distance to the object based on the total time between when the transducer 104 transmitted the sound to when the reflected echo signal was received. As the transducer 104 receives multiple reflected signals, the generated distances can be analyzed to create an image. The transducer 104 outputs the received reflected signals to the example T/R switch 108 via the example transducer node 103.

The example clamp 106 is a circuit that absorbs voltage glitches generated by enabling/disabling the example transmitter 102 and/or the example T/R switch 108 by providing a low impedance path for the glitch to be discharged to ground. Additionally, the example clamp 106 provides a high impedance during an off phase of the example clamp 106 to reduce signal distortion. The example clamp 106 is on (e.g., enabled) when the example transmitter 102 and/or the example T/R switch 108 transitions between power up to power down and vice versa, as further described in conjunction with FIG. 5. Additionally, during a transmit phase of the example ultrasound front end 100 (e.g., when the example clamp 106 is off), linearity of the example transmitter is not affected. The on phase and the off phase of the clamp 106 are controlled via on/off switches. An example circuit structure of the example clamp 106 is further described in conjunction with FIG. 3.

The example T/R switch 108 of FIG. 1 is powered down to block the high voltage pulse(s) from the example transmitter 102 during transmit stage and powered up to receive the reflected echo signals corresponding to the high voltage pulse(s). The example T/R switch 108 may include active and passive components to prevent the high voltage pulse(s) of the transmitter 102 from reaching the example receiver AFE 112 when disabled and provide low voltage reflected echo signal to the receiver AFE 112 when enabled.

The example switch controller 110 is a processor that controls power up/down switches of the example transmitter 102, the example clamp 106, and the example T/R switch 108. The example switch controller 110 enables and/or disables (e.g., opens and/or closes) the power up/down switches of the example transmitter 102 to power up/down the example transmitter 102. In some examples, the switch controller 110 may provide voltages to control the pulse(s) of the transmitter 102. The example switch controller 110 enables the on/off switches of the example clamp 106 to turn the clamp 106 on during transmitter 102 and/or T/R switch 108 transitions (e.g., on-to-off or off-to-on) and disables the on/off switches to turn the clamp 106 off during non-transitions. The example switch controller 110 controls an on/off switch of the example T/R switch 108 to enable and/or disable the example T/R switch 108.

The example receiver AFE 112 receives a reflected echo signal from the example transducer 104 via the example T/R switch 108 when the T/R switch 108 is enabled (e.g., powered up). The example receiver AFE 112 samples the reflected echo signal periodically or aperiodically to generate a digital samples of the reflected echo signal. In some examples, the receiver AFE 112 includes an analog to digital converter to convert the reflected echo signal into digital samples. The example receiver AFE 112 provides the digital samples to the example digital signal processor 114 for further processing.

The example digital signal processor 114 receives the digital samples from the example receiver AFE 112 and determines a distance corresponding to the digital samples. As the number of digital samples increases, the number of determined distances increases creating a depth of an object imaged through the reflected echo signals. The example digital signal processor 114 aggregates the different depth (e.g., distance) values for the imaged object to develop a two-dimensional or three-dimensional image of the object. The example digital signal processor 114 generates a signal corresponding the generated image for display on the example display 116. The example display 116 displays the generated image to a user.

During a transmit phase of the example ultrasound front end 100, the example transmitter 102 is enabled and the example clamp 106 and the example T/R switch 108 are disabled allowing the example transmitter 102 to provide high voltage pulse(s) to the example transducer 104 (e.g., via the example transducer node 103). During a receive phase of the example ultrasound front end 100, the example transmitter 102 and the example clamp 106 are disabled and the example T/R switch 108 is enabled allowing the T/R switch 108 to receive reflected echo signals allowing the example ultrasound front end 100 to determine distances of an object and/or generate an image of the object. During transitions between the transmit phase and the receive stage (e.g. a transient phase), the example transmitter 102 and the example T/R switch 108 are disabled and the example clamp 106 is enabled to absorb any glitch that may occur due to the transition.

Figure 2:
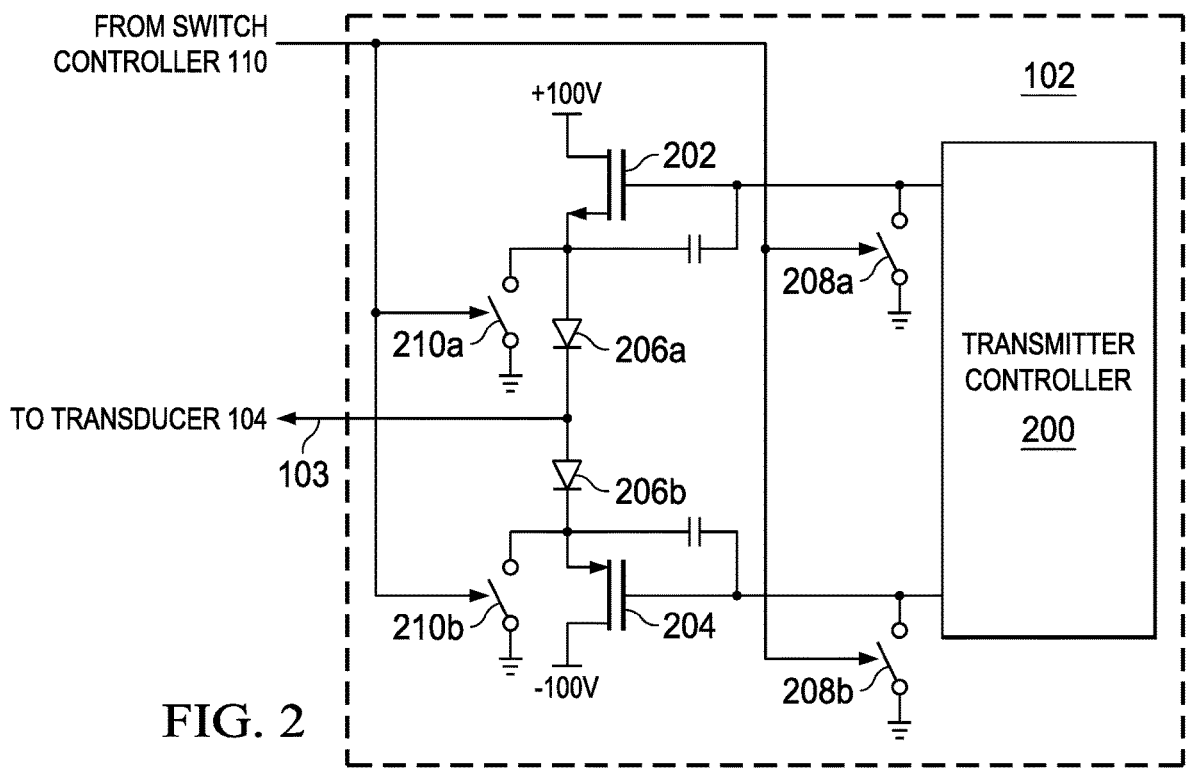
FIG. 2 is an example circuit diagram of a transmitter of FIG. 1.

FIG. 2 is an example circuit diagram of the example transmitter 102 disclosed herein to generate a high voltage (e.g., positive to negative 100 V) pulse via the example transducer node 103 of FIG. 1 during a transmit phase and provide a high impedance and power down during a receive phase. The example transmitter 102 includes an example transmitter controller 200, example transistors 202, 204, example series diodes 206a, 206b, example power up/down switches 208a, 208b, and example ground switches 210a, 210b. In the example transmitter 102, the example switches 208a, 208b, 210a, 210b are controlled by the example switch controller 110 of FIG. 1.

The example transmitter controller 200 controls the gates of the example transistors 202, 204 to enable and/or disable the transistors 202, 204 to increase and/or decrease the voltage at the example transducer node 103. In the illustrated example of FIG. 2, the example transistor 202 is a N-channel metal oxide field effect transistor (NMOS) and the example transistor 204 is a P-channel metal oxide field effect transistor (PMOS). For example, when the gate of the example NMOS transistor 202 is above a threshold voltage (e.g., 0.8V), the example NMOS transistor 202 will be enabled providing 100V (e.g., or any other voltage) to the example transducer node 103 via the example diode 206a. When the gate of the example PMOS transistor 204 is below a threshold voltage (e.g., −0.8V), the example PMOS transistor 204 will be enabled providing a −100V (e.g., or any other voltage) to the example transducer node 103 via the example diode 206b. During the transmit phase, the example transmitter controller 200 enables and/or disables the example transistors 202, 204 to provide pulse(s) between 100V and −100V. In some examples, the transmitter controller 200 may be combined with the example switch controller 110 of FIG. 1.

During a receive phase, the transmitter 102 provides a high impedance due to the configuration of the series diodes 206a, 206b (e.g., the configuration of the anodes and cathodes of the diodes 206a, 206b coupled in series at the example transducer node 103) that prevent current from entering the example transmitter 102 from the example transducer node 103. The example series diodes 206a, 206b are biased with quiescent current thereby eliminating, or otherwise reducing, any diode recovery issues associated with parallel diode configurations. Additionally, during the receive phase, the example switches 208a, 208b, 210a, 210b may be enabled (e.g., closed) to power down the example transmitter 102. The example power up/down switches 208a, 208b ground the gates of the example transistors 202, 204 to disable the example transistors 202, 204. When the example transistors 202, 204 are disabled, there is no path for the 100V voltage supply and/or the −100V voltage supply to travel, thereby powering down the example transmitter 102. The example ground switches 210a, 210b couple the example series diodes (e.g., via the anodes and cathodes of the example diodes) to ground to ensure that the example series diodes 206a, 206b do not conduct in the receive phase. Because the example series diodes 206a, 206b do not conduct and the reflected echo signal is around 500 mV peak to peak, the transmitter 102 becomes a high impedance transmitter and the reflected echo signal will travel directly to the example T/R switch 108.

Figure 3:
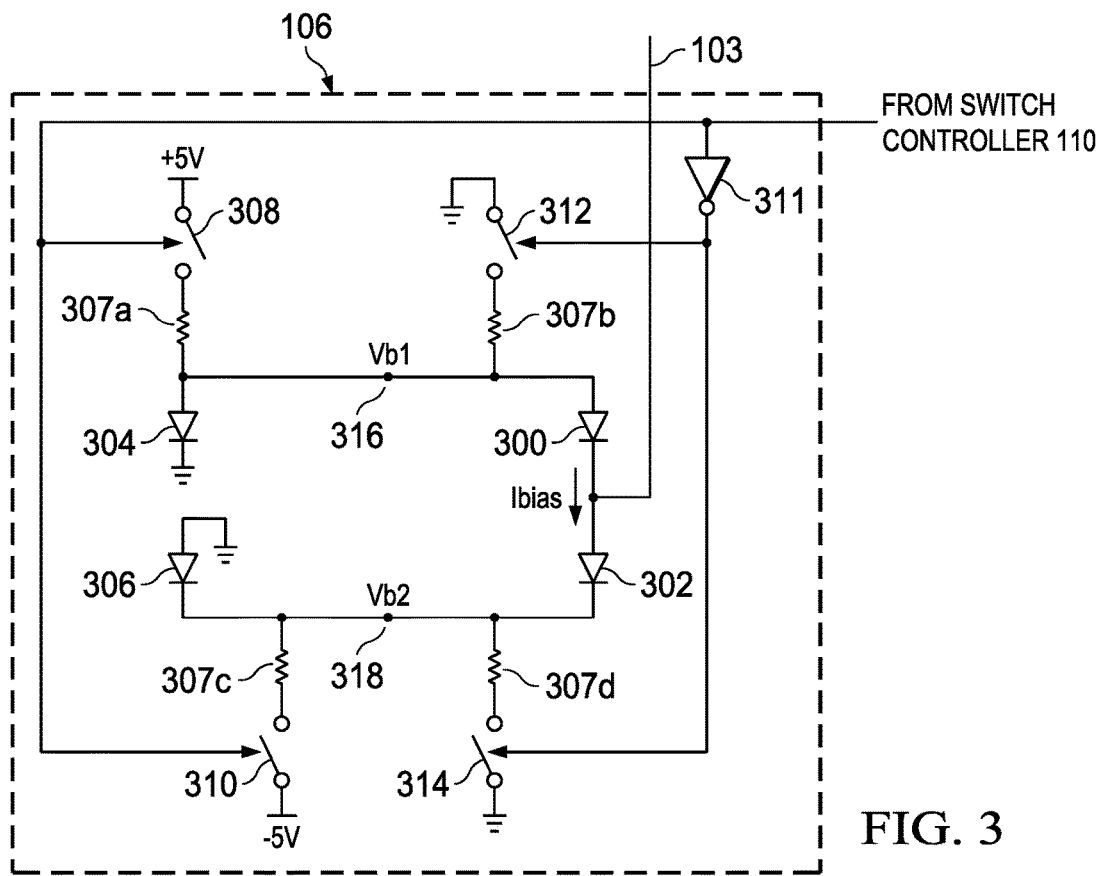
FIG. 3 is an example circuit diagram of a clamp of FIG. 1.

FIG. 3 is an example circuit diagram of the example clamp 106 disclosed herein to absorb a glitch at the example transducer node 103 of FIG. 1 during transition phases of the example transmitter 102 and/or the example T/R switch 108 of FIG. 1. The example clamp 106 includes example clamp diodes 300, 302 (e.g., coupled at the example transducer node 103), example bias diodes 304, 306, example bias resistors 307, example on switches 308, 310, an example inverting gate 311, example off switches 312, 314, an example node Vb1 316, and an example node Vb2 218. In the illustrated example clamp 106, the on/off switches 308, 310, 312, 314 are controlled by the example switch controller 110 of FIG. 1.

The example switch controller 110 controls the example switches 308, 310, 312, 314 to turn the example clamp 106 on or off during transient phases (e.g., between transmit phase and receive phase). To turn on the example clamp 106, the example switch controller 110 closes (e.g., enables) the example on switches 308, 310 and opens (e.g., disables) the example off switches 312, 314. To turn off the example clamp 106 the example switch controller 110 opens the example on switches 308, 310 and closes the example off switches 312, 314. In the illustrated example clamp 106 of FIG. 3, the example clamp 106 includes the example inverting gate 311. In some examples, the example on switches 308, 310 (e.g., combined with the example resistors 307a, 307c), and/or the example off switches 312, 314 (e.g., combined with the example resistors 307b, 307d) may be replaced with current sources that are controlled in a similar manner. For example, the example switch controller 110 may send a first voltage to on current sources (e.g., replacing the example on switches 308, 310) and a second voltage a second voltage to off current sources (e.g., replacing the example off switches 312, 314) to turn the example clamp 106 on. In such an example, the example switch controller 110 may send the second voltage to on current sources (e.g., replacing the example on switches 308, 310) and the first voltage a second voltage to off current sources (e.g., replacing the example off switches 312, 314) to turn the example clamp 106 off. The example inverting gate 311 allows the example switch controller 110 to send one signal to turn the example clamp 106 on and/or off via the example switches 308, 310, 312, 314. Alternatively, the example switch controller 110 may output to signals to the example clamp 106, one to control the example on switches 308, 310 and one to control the example off switches 312, 314. In such an example, the inverting gate 311 may not be necessary.

When the example clamp 106 is on (e.g., during transient state), the example clamp 106 provides a low impedance path to ground, thereby absorbing any glitch at the example transducer node 103. As described above, turning the example clamp 106 on includes enabling the example on switches 308, 310 and disabling the example off switches 312, 214. When the example switch 308 is enabled, 5V are provided, generating a bias current across the example bias resistor 307a and increasing the node voltage Vb1 316. The example bias resistor 307a corresponds to a resistance to cause the Vb1 316 to provide low resistance. Similarly, when the example switch 310 is enabled, −5V are provided, generating a bias current across the example bias resistor 307c and decreasing the example node voltage Vb2 318 to provide a low resistance. In some examples, the bias resistors 307a, 307c have the same resistance; thus, the node voltage Vb1 316 and the node voltage Vb2 are opposite voltages. The node voltage Vb1 316 and Vb2 318 are voltages set to a voltage (e.g., set via the resistance of the example bias resistors 307a, 307c) to allow the example Ibias 301 to flow through the example clamp diodes 300, 302 (e.g., Ibias is two times the product of the current through the example bias resistors 307a, 307c and the voltage at the example nodes Vb1, Vb2 316, 318). In some examples, the voltages at nodes Vb1, Vb2 316, 218 are chosen (e.g., based on the resistance of the biasing resistors 307a, 207c) to generate an on resistance of 20 ohms, corresponding to a 2 milliamp current through the example clamp diodes 300, 302. When the example clamp 106 is on, the example transducer node 103 is driven to a virtual ground because of the path generated from the 5V source to the −5V source, thereby absorbing (e.g., decreasing) any glitch caused by the transient state of the example transmitter 102 and/or the example T/R switch 108.

When the example clamp 106 is off (e.g., during transmit and/or receive phase), the example clamp 106 provides a high impedance input at the transducer node 103. As described above, turning the example clamp off 106 includes disabling the example on switches 308, 310 and enabling the example off switches 312, 214. When the example off switches 312, 314 are enabled, the example nodes Vb1 316 and Vb2 318 are biased at ground through a weak path to ground, thereby making nodes Vb1 316 and Vb2 318 high impedance floating nodes where the bias current through the example bias resistors 207b, 307c is substantially zero. Biasing the nodes 316, 218 to ground allows the transmitter to swing the voltage at the example transducer node 103 from 100V to −100V without affecting the linearity of the swinging voltage, thereby reducing signal distortion.

Because the example clamp 106 is enabled and/or disabled via control of the example switches 308, 310, 312, 314, the transient state of the example clamp 106 may also create a glitch. However, the glitch caused by opening and/or closing the example switches 308, 310, 312, 314 is absorbed by the clamp 106 itself due to the fully differential structure of the clamp 106. For example, while transitioning the clamp 106 from on to off, a glitch at the example node Vb1 316 may be output to the example transducer node 103 via the example diode 300; however, the glitch will be cancelled by the example diode 302, thereby eliminating, or otherwise reducing, the glitch at the example transducer node 103. Additionally, parasitic capacitance at the intersection of the example diodes 300, 302, 304, 306 at the example nodes Vb1 316 and Vb2 318 is small. Accordingly, the recovery times of the example diodes 300, 302, 304, 306 is fast, providing quick on/off times for enabling and/or disabling the example clamp 106.

While example manners of implementing the example switch controller 110 and/or the example transmitter controller 200 are illustrated in FIGS. 1 and 2, elements, processes and/or devices illustrated in FIGS. 1 and 2 may be combined, divided, re-arranged, omitted, eliminated and/or implemented in any other way. Further, the example switch controller 110 and/or the example transmitter controller 200 of FIGS. 1 and 2, may be implemented by hardware, machine readable instructions, software, firmware and/or any combination of hardware, machine readable instructions, software and/or firmware. Thus, for example, any of the example switch controller 110 and/or the example transmitter controller 200 of FIGS. 1 and 2, could be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example switch controller 110 and/or the example transmitter controller 200 of FIGS. 1 and 2, is/are hereby expressly defined to include a tangible computer readable storage device or storage disk such as a memory, a digital versatile disk (DVD), a compact disk (CD), a Blu-ray disk, etc. storing the software and/or firmware. Further still, the example switch controller 110 and/or the example transmitter controller 200 of FIGS. 1 and 2 includes elements, processes and/or devices in addition to, or instead of, those illustrated in FIGS. 1 and 2, and/or may include more than one of any or all of the illustrated elements, processes and devices.

Figure 4:
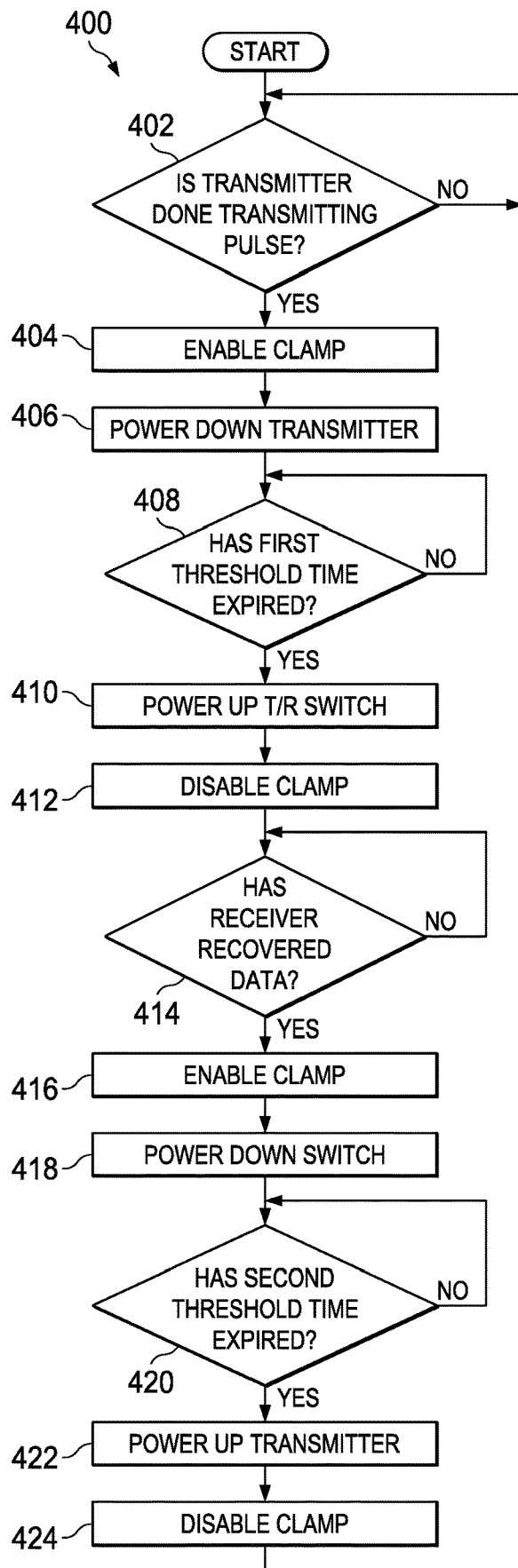
FIG. 4 is flowchart representative of example machine readable instructions that may be executed to implement a switch controller of FIG. 110.

A flowchart representative of example machine readable instructions for implementing the example switch controller 110 and/or the example transmitter controller 200 of FIGS. 1 and 2 is shown in FIG. 4. In the examples, the machine readable instructions comprise a program for execution by a processor such as the processor 612 shown in the example processor platform 600 discussed below in connection with FIG. 6. The program may be embodied in machine readable instructions stored on a tangible computer readable storage medium such as a CD-ROM, a floppy disk, a hard drive, a digital versatile disk (DVD), a Blu-ray disk, or a memory associated with the processor 612, but the entire program and/or parts thereof could alternatively be executed by a device other than the processor 612 and/or embodied in firmware or dedicated hardware. Further, although the example program is described with reference to the flowchart illustrated in FIG. 4, many other methods of implementing the example switch controller 110 and/or the example transmitter controller 200 of FIGS. 1 and 2 may alternatively be used. For example, the order of execution of the blocks may be changed, and/or some of the blocks described may be changed, eliminated, or combined.

As mentioned above, the example process of FIG. 4 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIG. 4 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 4 is an example flowchart 400 representative of example machine readable instructions that may be executed by the example switch controller 110 of FIG. 1 to transition between the transmit phase and the receive phase of the example ultrasound front end 100 while reducing a glitch associated with transitions between the phases. Although the flowchart 400 is described in conjunction with the example ultrasound front end 100 of FIG. 1, the flowchart 400 used to implement any type of ultrasound front end.

Initially, the example switch controller 110 powers up the example transmitter 102 by disabling the example switches 208a, 208b, 210a, 210b. The example switch controller 110 powers up the example transmitter 102 to initiate the transmit phase of the example ultrasound front end 100. As described above in conjunction with FIG. 1, during a transmit phase, the example switch controller 110 enables the example transmitter 102 and disables the example clamp 106 and the example T/R switch 108. Once the example switches 208a, 208b, 210a, 210b are disabled (e.g., opened), the example transmitter controller 200 applies voltages to the gates of the example transistors 202, 204 to output a high pulse and/or low pulse on the example transducer node 103. In some examples, the example switch controller 110 is the example transmitter controller 200. In such examples, the switch controller 110 applies voltage to the gates of the example transistors 202, 204.

At block 402, the example switch controller 110 determines if the example transmitter 102 is done transmitting the voltage pulse(s) to the example transducer 104 via the transducer node 103. In some examples, the switch controller 110 makes the determination based on a timer (e.g., when the transmit phase corresponds to a duration of time (10 microseconds)). In some examples, the example transmitter 102 transmits a signal to the example switch controller 110 when the transmitter 102 is done transmitting the pulse(s). If the example switch controller 110 determines that the example transmitter 102 is not done transmitting the voltage pulse(s) (e.g., the example ultrasound front end 100 is still in the transmit phase), the example switch controller 110 maintains control of the example switches 208a, 208b, 210a, 210b to keep the switches 208a, 208b, 210a, 210b disabled/closed until the transmit phase ends. If the example switch controller 110 determines that the example switch controller 110 determines that the example transmitter 102 is done transmitting a pulse (e.g., the example ultrasound front end 100 is ending the transmit phase and will transition into a receive phase), the example switch controller 110 enables the example clamp 106 (block 404). As described above in conjunction with FIG. 3, the example switch controller 110 enables the example clamp 106 by enabling the example on switches 308, 310 and disabling the example off switches 312, 314. Enabling the example clamp 106 adjusts the clamp 106 from a high impedance circuit at the example transducer node 103 to a low impedance circuit at the example transducer node 103, thereby allowing any glitch produced by the example transmitter 102 to be absorbed (e.g., discharged to ground).

At block 406, the example switch controller 110 powers down the example transmitter 102 by enabling (e.g., closing) the example switches 208a, 208b, 210a, 210b. As described above in conjunction with FIG. 2, the example power up/down switches 208a, 208b provide a ground voltage to the gates of the example transistors 202, 204. Applying a ground voltage to the gates of the example transistors 202, 204 turns the transistors 202, 204 off to eliminate a path for the 100V and/or the −100V power supplies, thereby powering down the example transmitter 102. The example ground switches 210a, 210b provide a ground voltage to the example diodes 206a, 206b ensuring that the example diodes 206a, 206b do not conduct during the receive phase. When the example diodes 206a, 206b do not conduct, the example transmitter 102 becomes a high impedance circuit at the example transducer node 103 (e.g., reducing reflected echo signal distortion).

At block 408, the example switch controller 110 determines if a first threshold time (e.g., 1 micro second) has expired. The first threshold time correspond to the transient time between the transmit phase and the receive phase. The first threshold time provides sufficient time for the example clamp 106 to absorb any glitch produced by the example transmitter 102 and/or any glitch produced by the example clamp 106 itself. If the example switch controller 110 determines that the first threshold time has not expired, the example switch controller 110 continues to control the switches of the example transmitter 102, the example clamp 106, and the example T/R switch 108 to keep the transmitter 102 disabled, the example clamp 106 enabled, and the example T/R switch 108 disabled.

When the first threshold time expires (e.g., after the transient phase), the example switch controller 110 powers up the example T/R switch 108 to initiate the receive phase (block 410). At block 412, the example switch controller 110 disables the example clamp 106. The example switch controller 110 disables the example clamp 106 by disabling the example on switches 308, 310 and enabling the example off switches 312, 214. As described above in conjunction with FIG. 3, enabling the example clamp 106 allows the clamp 106 to provide a high impedance at the example transducer node 103. Such a high impedance allows the reflected echo signal received by the transducer to be received by the example receiver analog front end 112 via the example T/R switch 108 without being degraded by the example clamp 106.

At block 414, the example switch controller 110 determines if the example receiver analog front end 112 has fully received the reflected echo signal. In some examples, the switch controller 110 makes the determination based on a timer (e.g., when the receive phase corresponds to a duration of time (84 microseconds)). In some examples, the receiver analog front end 112 transmits a signal to the example switch controller 110 when the reflected echo signal has been fully received. If the example switch controller 110 determines that the example receiver analog front end 112 has not fully received the reflected echo signal, the example switch controller 110 continues to enable the example the example T/R switch 108 until the reflected echo signal is received by the example receiver analog front end 112. If the example switch controller 110 determines that the example receiver front end 112 has fully received the reflected echo signal, the example switch controller 110 enables the example clamp 106 (block 416) to absorb any glitch corresponding to the transition back to the transmit phase. At block 418, the example switch controller 110 powers down the example T/R switch 108 (e.g., ending the example receive phase).

At block 420, the example switch controller 110 determines if a second threshold time (e.g., 5 micro second) has expired. The second threshold time correspond to the transient time between the receive phase and the transmit phase. The second threshold time provides sufficient time for the example clamp 106 to absorb any glitch produced by the example T/R switch 108 and/or any glitch produced by the example clamp 106 itself. If the example switch controller 110 determines that the second threshold time has not expired, the example switch controller 110 continues to control the switches of the example transmitter 102, the example clamp 106, and the example T/R switch 108 to keep the transmitter 102 and the example T/R switch 108 disabled and the example clamp 106 enabled. When the example switch controller 110 determines that the second threshold time has expired, the example switch controller 110 powers up the example transmitter 102 (block 422) (e.g., by disabling the example switches 208a, 208b, 210a, 210b). At block 424, the example switch controller 110 disables the example clamp 109 (e.g., by disabling the example on switches 308, 310 and enabling the example off switches 312, 214) and the process is repeated.

Figure 5:
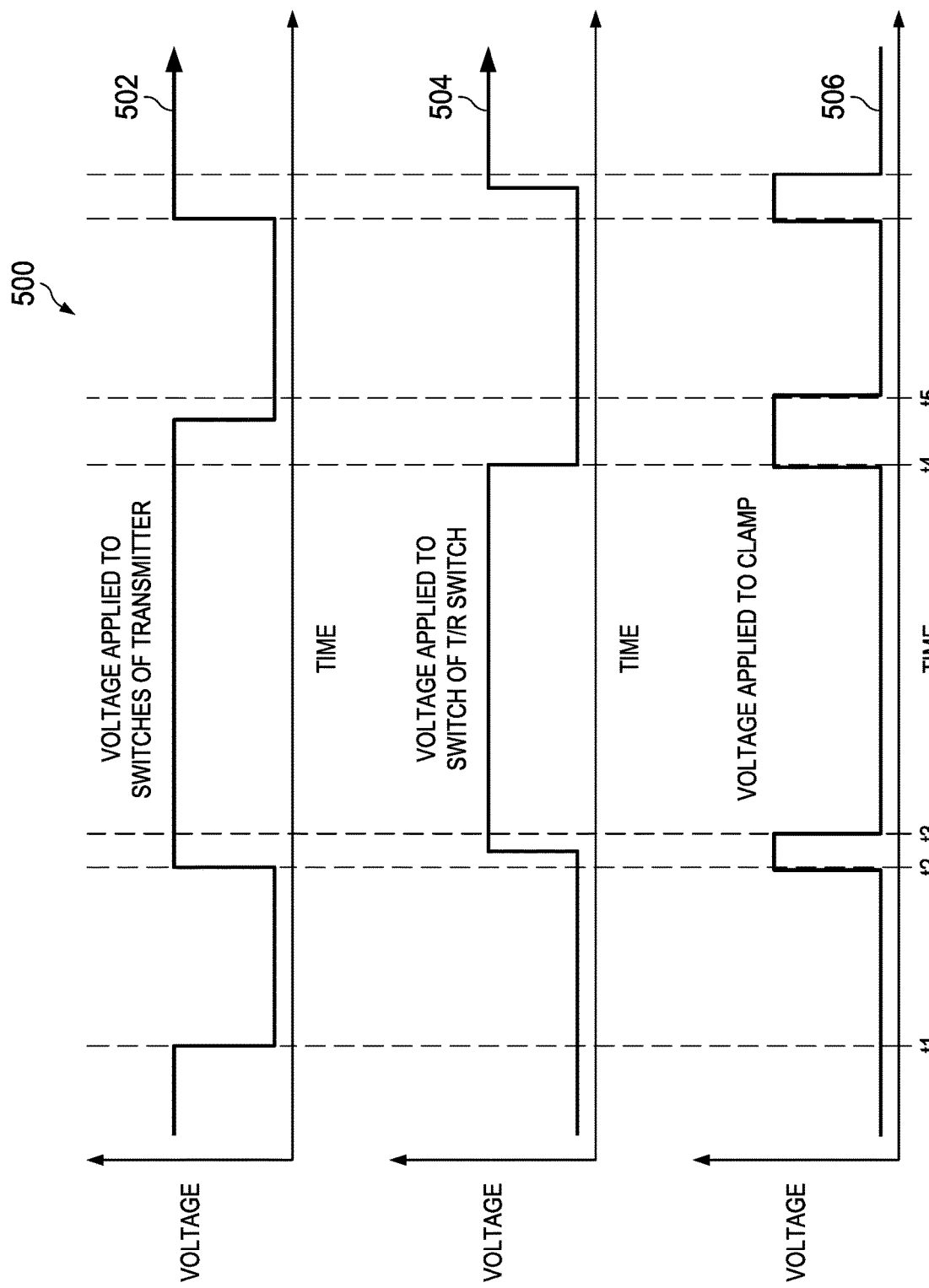
FIG. 5 is a graph illustrating control of the example transmitter, the example clamp, and an example transmitter/receiver switch of FIG. 1.

FIG. 5 is an example graph 500 illustrating control of the example transmitter 102, the example clamp 106, and a switch of the example T/R switch 108 of FIG. 1. The example graph 500 includes an example transmitter control signal 502, an example T/R switch control signal 504, and an example clamp control signal 506. The example transmitter control signal 502 corresponds to control of the example switches 208a, 208b, 210a, 210b of FIG. 2 to enable and/or disable the example transmitter 102. The example T/R switch 108 corresponds to control of the example T/R switch 108 of FIG. 1 to enable and/or disable the example T/R switch 108. The example clamp control signal 506 corresponds to control of the example switches 308, 310, 312, 314 to enable and/or disable the example clamp 106 of FIG. 3.

At time t1, the example transmitter control signal 502 goes low indicating that the powering up of the example transmitter 102. As described above in conjunction with FIG. 2, the example switch controller 110 powers up (e.g., enables) the example transmitter 102 by disabling (e.g., opening) the example switches 208a, 208b, 210a, 210b. The example transmitter control signal 502 remains low for a duration of time (e.g., 10 microseconds) to allow the example transmitter 102 to output a pulse(s) to the example transducer 104 via the example transducer node 103.

At time t2, when the transmitter 102 finishing transmitting the pulse(s) to the example transducer 104, the example clamp control signal 506 goes high indicating the enabling of the example clamp 106. In some examples, the clamp control signal 506 may go high slightly before time t2. As described above in conjunction with FIG. 3, the example switch controller 110 powers up the example clamp 106 by enabling (e.g., closing) the example on switch 308, 310 and disabling (e.g., opening) the example off switches 312, 314. Enabling the example clamp 106 changes the clamp 106 from a high impedance circuit to a low impedance circuit providing a path to ground to absorb any glitch caused by powering down the example transmitter 102. Additionally at time t2 (or shortly thereafter), the example transmitter signal 502 goes high indicating the powering down (e.g., disabling) of the example transmitter 102. The example switch controller 110 powers down the example transmitter 102 by enabling the example switches 208a, 208b, 210a, 210b, to adjust the example transmitter into a high impedance circuit. The example clamp control signal 506 remains high for a duration of time (e.g., 1 microsecond) for the clamp to absorb the glitch.

Before time t3 (e.g., between time t2 and time t3), the example T/R switch control signal 504 goes high, indicating the enabling of the example T/R switch 108 (e.g., via a control signal from the example switch controller 110). At time t3, the example clamp control signal 506 goes low indicating the disabling of the example clamp 106 (e.g., by disabling the example on switches 308, 310 and enabling the example off switches 312, 314), thereby adjusting the example clamp 106 from a low impedance circuit to a high impedance circuit. After time t3, the example T/R switch control signal 504 remains high for a duration of time (e.g., 84 microseconds) to allow the example receiver analog front end 112 of FIG. 1 to receive a reflected echo signal in response to the pulse generated by the example transmitter 102 between times t1 and t2.

At time t4, after the example receiver analog front end 112 has received the reflected echo signal, the example T/R switch control signal 504 goes low, indicating the disabling of the example T/R switch 108. Additionally at or slightly before time t4, the example clamp control signal 506 goes high indicating the enabling of the example clamp 106, adjusting the clamp 106 from a high impedance circuit to a low impedance circuit to absorb a glitch produced by the disabling of the example T/R switch 108. The example clamp control signal 506 remains high for a second duration of time (e.g. 5 microseconds) for the example clamp 106 to absorb the glitch. Before time t5 (e.g., between time t4 and t5), the example transmitter signal 502 goes low to power up the example transmitter 102. At time t5, the example clamp control signal 506 goes low and the process repeats for an additional pulse.

Figure 6:
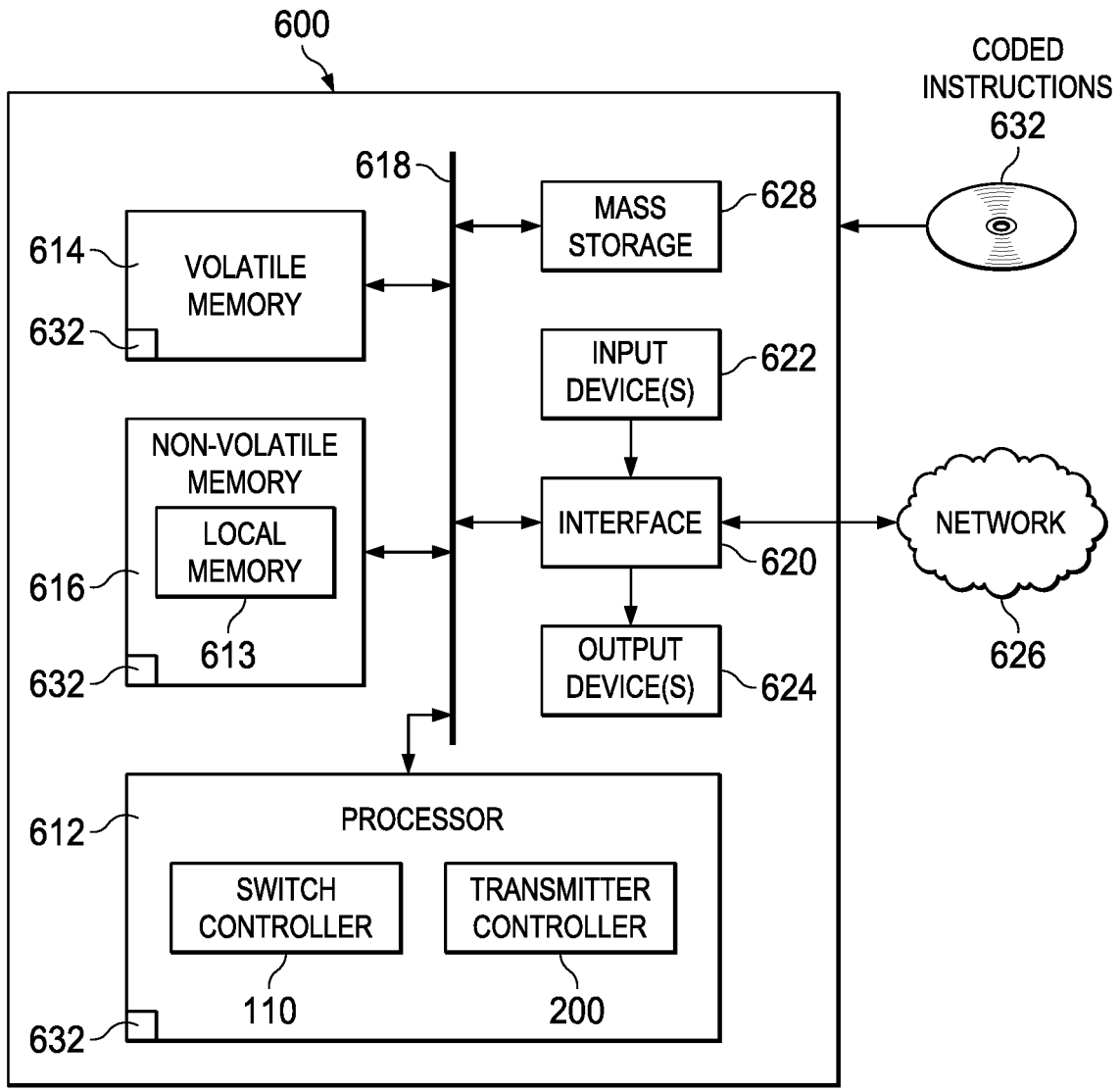
FIG. 6 is an example processor platform that may execute the example computer readable instructions of FIG. 4 to implement an example switch controller of FIG. 1.

FIG. 6 is a block diagram of an example processor platform 600 capable of executing the instructions of FIG. 4 to implement the example switch controller 110 and/or the example transmitter controller 200 of FIGS. 1 and 2. The processor platform 600 can be, for example, a server, a personal computer, a mobile device (e.g., a cell phone, a smart phone, a tablet such as an iPad™), a personal digital assistant (PDA), an Internet appliance, or any other type of computing device.

The processor platform 600 of the illustrated example includes a processor 612. The processor 612 of the illustrated example is hardware. For example, the processor 612 can be implemented by integrated circuits, logic circuits, microprocessors or controllers from any desired family or manufacturer.

The processor 612 of the illustrated example includes the example memory 613 (e.g., a cache). The example processor 612 of FIG. 6 executes the instructions of FIG. 4 to implement the example switch controller 110 and/or the example transmitter controller 200 of FIGS. 1 and 2. The processor 612 of the illustrated example is in communication with a main memory including a volatile memory 614 and a non-volatile memory 616 via a bus 618. The volatile memory 614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 616 may be implemented by flash memory and/or any other desired type of memory device. Access to the main memory 614, 616 is controlled by a memory controller.

The processor platform 600 of the illustrated example also includes an interface circuit 620. The interface circuit 620 may be implemented by any type of interface standard, such as an Ethernet interface, a universal serial bus (USB), and/or a PCI express interface.

In the illustrated example, one or more input devices 622 are connected to the interface circuit 620. The input device(s) 622 permit(s) a user to enter data and commands into the processor 612. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 624 are also connected to the interface circuit 620 of the illustrated example. The output devices 624 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 620 of the illustrated example, thus, typically includes a graphics driver card, a graphics driver chip or a graphics driver processor.

The interface circuit 620 of the illustrated example also includes a communication device such as a transmitter, a receiver, a transceiver, a modem and/or network interface card to facilitate exchange of data with external machines (e.g., computing devices of any kind) via a network 626 (e.g., an Ethernet connection, a digital subscriber line (DSL), a telephone line, coaxial cable, a cellular telephone system, etc.).

The processor platform 600 of the illustrated example also includes one or more mass storage devices 628 for storing software and/or data. Examples of such mass storage devices 628 include floppy disk drives, hard drive disks, compact disk drives, Blu-ray disk drives, RAID systems, and digital versatile disk (DVD) drives.

The coded instructions 632 of FIG. 4 may be stored in the mass storage device 628, in the volatile memory 614, in the non-volatile memory 616, and/or on a removable tangible computer readable storage medium such as a CD or DVD.

From the foregoing, it would be appreciated that the above disclosed method, apparatus, and articles of manufacture reduce a glitch during a transient phase of an ultrasound front end. Examples disclosed herein includes a transmitter to provide a voltage pulse during a transmit phase and to act as a high impedance circuit during a receive phase via series diodes that reduce signal distortion. Examples disclosed herein further include a clamp to provide a low impedance path for absorbing glitches during transient phases and to provide a high impedance path during transmit and/or receive phase to reduce signal distortion. Conventional ultrasound front ends include parallel diodes at the output of the transmitter to reduce a glitch and do not include a clamp. Additionally, conventional ultrasound front ends do not power down the transmitter when not in use (e.g., in the receive phase) to avoid additional glitches. Using example disclosed herein, the transmitter and clamp reduce the glitch while limiting signal distortion. Additionally, using example disclosed herein, the transmitter can be powered down when not in use without producing an additional glitch. Accordingly, example disclosed herein reduce the glitch from 50 millivolts to 15 millivolts while conserving power.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An ultrasound front end comprising:
    a transducer to (A) output a signal during a transmit phase and (B) receive a reflected signal corresponding to the signal during a receive phase;
    a receiver switch coupled to the transducer at a first node, the receiver switch to (A) open during the transmit phase and (B) close during the receive phase; and
    a clamp coupled to the transducer at the first node, the clamp to provide a high impedance during the transmit phase and the receive phase and provide a low impedance during a transient phase.

2. The ultrasound front end of claim 1, wherein the transient phase occurs during a first transition from the transmit phase to the receive phase and during a second transition from the receive phase to the transmit phase.

3. The ultrasound front end of claim 1, further including a transmitter coupled to the transducer at the first node, the transmitter to transmit a voltage pulse to the transducer during the transmit phase, the signal output by the transducer corresponding to the voltage pulse.

4. The ultrasound front end of claim 3, wherein the transmitter is to provide a high impedance from the first node to ground during the receive phase.

5. The ultrasound front end of claim 3, wherein the transmitter is to power down during the transient phase and the receive phase.

6. The ultrasound front end of claim 3, wherein the transmitter includes:
    a first diode coupled in series to a second diode at the first node;
    a first switch coupled to a first gate of a first transistor, the first transistor to, when enabled, provide a first voltage to the first node;
    a second switch coupled to an anode of the first diode;
    a third switch coupled to a second gate of a second transistor, the second transistor to, when enabled, provide a second voltage to the first node; and
    a third switch coupled to a cathode of the second diode.

7. The ultrasound front end of claim 6, further including a controller to:
    close the first and third switches during the transmit phase to power up the transmitter;
    open the first and third switches during the receive phase to power down the transmitter; and
    close the second and fourth switches during the transmit phase to ensure that the first and second diodes conduct.

8. The ultrasound front end of claim 7, wherein the first and second diodes provide a high impedance during the receive phase.

9. The ultrasound front end of claim 1, wherein the clamp includes:
    a first on switch coupled to a first voltage source
    a second on switch coupled to a second voltage source;
    a first off switch coupled to ground;
    a second off switch coupled to ground; and
    a first diode coupled in series with a second diode at the first node.

10. The ultrasound front end of claim 9, further including a controller to:
    enable the clamp by closing the first and second on switches and opening the first and second off switches during the transient phase; and
    disable the clamp by opening the first and second on switches and closing the first and second off switches during the transmit phase and the receive phase.

11. The ultrasound front end of claim 10, wherein:
    enabling the clamp provides a low impedance path to ground to absorb a glitch; and
    disabling the clamp provides a high impedance path to prevent signal distortion.

12. The ultrasound front end of claim 11, wherein the first and second diodes absorb a glitch generated when at least one of the enabling or the disabling of the clamp.

13. The ultrasound front end of claim 1, wherein the clamp is to absorb a glitch at the first node during the transient phase.

* * * * *